United States Patent [19]

Frascotti et al.

[11] Patent Number: 5,721,137
[45] Date of Patent: Feb. 24, 1998

[54] PLASMID VECTOR AND ITS USE FOR THE PRODUCTION OF HETEROLOGOUS PROTEINS

[75] Inventors: Gianni Frascotti, Milan; Guido Grandi, Segrate, both of Italy

[73] Assignee: Eniricerche S.p.A., Milan, Italy

[21] Appl. No.: 400,864

[22] Filed: Mar. 8, 1995

[30] Foreign Application Priority Data

Apr. 15, 1994 [IT] Italy .................... MI94A0727

[51] Int. Cl.⁶ .................... C12N 15/70; C12N 15/75; C12N 15/11; C12P 21/02
[52] U.S. Cl. ............... 435/320.1; 435/69.1; 435/252.31; 435/252.33
[58] Field of Search .................. 435/69.1, 252.31, 435/252.33, 320.1

[56] References Cited

FOREIGN PATENT DOCUMENTS 0245218  11/1987  European Pat. Off. ........ C12N 15/00
0281530   9/1988  European Pat. Off. ........ C12N 15/00

OTHER PUBLICATIONS

New England Biolabs 1992 Catalog, p. 160.

*Primary Examiner*—David Guzo
*Assistant Examiner*—Nancy J. Degen
*Attorney, Agent, or Firm*—Oblon, Spivak, McClelland, Maier & Neustadt, P.C.

[57] ABSTRACT

A new plasmid vector operable in *Escherichia coli* and *Bacillus subtilis*, comprising a synthetic promoter capable of directing with great efficiency the expression of the heterologous gene under its control is described. This vector which has a high stability in transformed strains is particularly useful for the production of heterologous proteins in *Escherichia coli* and/or *Bacillus subtilis*.

6 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTAGAAAAAT TTATTTGCTT TCAGGAAAAT TTTTTATGTA TAATAGATT    49

( 2 ) INFORMATION FOR SEQ ID NO:2:

( i ) SEQUENCE CHARACTERISTICS:
      ( A ) LENGTH: 125 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

CTAGAAAAAT TTATTTGCTT TCAGGAAAAT TTTTTATGTA TAATAGATTC ATAAATTTGA    60

GAGCTCAAAG GAGGAATTCG AGCTCGGTAC CCGGGGATCC TCTAGAGTCG ACCTGCAGGC    120

ATGCA    125

( 2 ) INFORMATION FOR SEQ ID NO:3:

( i ) SEQUENCE CHARACTERISTICS:
      ( A ) LENGTH: 126 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

TTTTTAAATA AACGAAAGTC CTTTTAAAAA ATACATATTA TCTAAGTATT TAAACTCTCG    60

AGTTTCCTCC TTAAGCTCGA GCCATGGGCC CCTAGGAGAT CTCAGCTGGA CGTCCGTACG    120

TTCGAA    126

( 2 ) INFORMATION FOR SEQ ID NO:4:

( i ) SEQUENCE CHARACTERISTICS:
      ( A ) LENGTH: 57 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:4:

GAATTCGAGC TCGGTACCCG GGATCCTCT AGAGTCGACC TGCAGGCATG CAAGCTT    57

PLASMID VECTOR AND ITS USE FOR THE PRODUCTION OF HETEROLOGOUS PROTEINS

The present invention relates to a plasmid vector, microorganisms transformed with said vector and their use in the preparation of heterologous proteins.

More particularly, the present invention relates to a plasmid vector stable in *Escherichia coli* and/or *Bacillus subtilis*, comprising a synthetic promoter capable of directing with great efficiency the expression of a heterologous gene put under its control.

In the art, it is already known to prepare proteins by fermentation processes which use particular production systems, this term meaning the combination of an expression vector containing the gene which encodes for the protein with the host which contains it.

From an industrial point of view, an ideal production system should enable the preparation of an easily purifiable recombinant product, in high yields, with a biological activity identical to that of the natural protein and at economically interesting costs. Such a system should consist of:

1) a vector which contains strong regulation elements (promoter, RBS and terminator), i.e. capable of directing an efficient expression of a heterologous gene; which is present in the cells in multiple copies and is stably maintained inside the cells to allow a high production of the particular product; and 2) a host which correctly carries out the instructions supplied for the heterologous gene thus enabling a product to be obtaind which is identical to the natural one; which is suitable for a culture on a commercial scale, i.e. resistant, capable of multiplying with high densities and undemanding with respect to the requirement of nutritive elements.

It has now been found that these requirements of the known art can be satisfied by the plasmid vector of the present invention.

In accordance with this, a first aspect of the present invention relates to a plasmid vector stable in *Escherichia coli* and *Bacillus subtilis* characterized in that it contains a synthetic promoter capable of directing with great efficiency the expression of a heterologous gene.

A further aspect of the present invention relates to a microorganism selected from *Escherichia coli* or *Bacillus subtilis* transformed with said plasmid vector.

Yet another aspect of the present invention relates to a process for the production of a particular heterologous protein by the fermentation of a microorganism selected from *Escherichia coli* or *Bacillus subtilis* transformed with said plasmid vector.

In particular, the plasmid vector of the present invention comprises:

1. the replication origins operable in *B.subtilis* and *E.coli*;
2. the genes which encode the selection of strains transformed with said plasmid vector;
3. a synthetic promoter having the sequence (SEQ ID NO:1)

```
        XbaI                    -35
    5'CTAGAAAAAT TTATTTGCTT TCAGGAAAAT
                    -10
    TTTTTATGTA TAATAGATT 3'
```

4. a ribosome binding site;
5. a multiple cloning site downstream the promoter useful for the insertion of the heterologous genes.
6. the terminator $t_o$ of the lambda bacteriophage.

The plasmid vector, indicated hereafter as pSM671, of the present invention is obtained by a process which comprises:

(a) synthesizing a polynucleotide comprising a synthetic promoter having the above sequence, the bond site of the mRNA at the ribosome (RBS) and the multiple cloning site (MCS) of the plasmid pUC18;

(b) isolating from the plasmid pSM143 the fragment HindIII-XbaI of about 5700 bp containing the replication origins operable in *E.coli* and *B.subtilis* and the gene resistant to Kanamycin;

(c) ligating the polynucleotide to the fragment obtained in step (b) and isolating the plasmid pSM143-A;

(d) introducing down stream the multiple cloning site of the plasmid pSM143-A a fragment of about 1000 bp containing the Cat gene (chloramphenicol acetyl transpherase) and the synthetic terminator $t_o$ of the lambda bacteriophage; and finally (e) isolating the plasmid vector pSM671 by the selection of *E.coli* cells transformed with the ligase mixture obtained in step d).

The polynucleotide of the present invention has the sequence (SEQ ID NOS:2 and 3)

```
        XbaI              -35                       -10
5'CTAGAAAAATTTATTTGCTTTCAGGAAAATTTTTTATGTATAATAGA-
3'      TTTTTAAATAAACGAAAGTCCTTTTAAAAAATACATATTATCT

RBS              MCS pUC18
TTCATAAATTTGAGAGCTCAAAGGAGGAATTCGAGCTCGGTACCCGGGG-
AAGTATTTAAACTCTCGAGTTTCCTCCTTAAGCTCGAGCCATGGGCCCC

EcoRI
ATCCTCTAGAGTCGACCTGCAGGCATGCA 3'
TAGGAGATCTCAGCTGGACGTCCGTACGTTCGAA 5'
                                    HindIII
```

Said polynucleotide, which comprises restriction sites useful for the bond with the fragment isolated from pSM143 (ATCC 53038), was synthesized using a commercial apparatus operating according to the conventional methods.

The vector pSM143 was digested with the restriction enzymes HindIII and XbaI obtaining two fragments, of about 5700 bp and 1650 bp respectively, the latter containing the promoter region of resistance to erythromycin of pE194 and the Bla gene which gives resistance to Ampicillin.

The 5700 bp fragment, containing the replication origins operable in *E.coli* and *B.subtilis* and the gene for resistance to Kanamycin, was then purified and ligated to the synthetic polynucleotide having the above sequence under such conditions as to facilitate the condensation of a single fragment to each molecule of polynucleotide. The ligation reaction was carried out with the conventional techniques in the presence of the enzyme T4 DNA ligase. The ligase mixture was used to transform E.coli cells made competent as described for example by Dagert, M. and Ehrlich (Gene (1979), 6:23).

The plasmid DNA was extracted from one of the positive colonies selected on a medium containing Kanamycin and sequenced according to the method of Sanger F. et al. (Proc. Natl. Acad. Sci. USA (1977), 74: 5463).

It was therefore possible to verify the exact insertion of the synthetic fragment into pSM143, in the place of the region which comprised the promoter of the resistance to erythromycin and the Bla gene. The new plasmid was called pSM143-A.

The DNA fragment of about 1000 bp, containing the Cat gene, which gives resistance to Chloramphenicol, without its own promoter and terminator $t_O$ of the lambda bacteriophage, was then isolated from the plasmid pSM213 described in Italian patent 19.551 A/87. This fragment was ligated to plasmid pSM143-A digested with the restriction enzymes XhoI and HindIII. The ligase mixture was used to transform E.coli cells made competent as described for example by Dagert, M. and Ehrlich (Gene (1979), 6:23).

A plasmid was extracted from one of the positive colonies (Km$^r$Cm$^r$) selected on a medium containing Kanamycin and Chloramphenicol, which upon sequence analysis showed the expected characteristics, or the presence of the synthetic promoter, the RBS site, the multiple cloning site of puC18, the Cat gene, the lambda terminator $t_O$ and double resistance to the antibiotics Kanamycin and Chloramphenicol. This plasmid was called pSM671.

The segregational and structural stability of the vector pSM671 in E.coli and B.subtilis was determined operating as described in example 2. The results showed that the plasmid is maintained in more than 95% of the cellular population even after subsequent passages in culture, thus showing a considerable segregational stability.

In addition analysis of the plasmids isolated from the transformed strains showed that even after various generations of liquid culture said plasmid remains structurally stable both in E.coli and in B.subtilis.

The plasmid vector pSM671 of the present invention can be used for the expression of genes which encode a prokaryotic polypeptide such as, for example, an enzyme such as hydantoinase, carbamylase, α-amylase, β-amylase, isoamylase, or an eukaryotic polypeptide selected for example from interleukin, natural antagonist of IL-1β, growth hormone, interferon, recombinant antibodies, etc..

The capacity of the promoter to direct a high expression of the heterologous gene placed down stream was verified by the insertion into the multiple cloning site (MCS) of genes encoding for proteins of interest such as: carbamylase, a recombinant single chain antibody, human growth hormone (hGH), interleukin-1β (IL-1β) and natural antagonist of IL-1β(IL-1rα). Strains of B.subtilis and E.coli transformed with said recombinant DNA molecules were then cultivated. The results showed the presence of these heterologous proteins which are expressed in high quantities in the two microorganisms (>5% of the total proteins).

The plasmid vector pSM671 was deposited on Apr. 13, 1994 at the Centraalbureau Voor Schimmelcultures Oosterstraat 1, P.O. Box 273, 3740 AG BAARN, The Netherlands, as *Escherichia coli* SMC309 where it received the number CBS 205.94.

A) Restriction map of the plasmid pSM143
B) Restriction map of the plasmid pSM213

FIG. 2

Restriction map of the plasmid pSM671 (SEQ ID NO:4)

FIG. 3

A) Plasmid DNA extracted, after 16 hours of culture, from 3 clones of E.coli 71/18 and cut with the restriction enzyme BamHI.

1–14) 1 Kb DNA ladder; 2–4) clones 1, 2 and 3: preculture; 5–7) clones 1, 2 and 3: I culture; 8–10) clones 1, 2 and 3: II culture; 11–13) clones 1, 2 and 3: III culture.

B) Plasmid DNA extracted, after 16 hours of culture, from 3 clones of B.subtilis SMS003 and cut with the restriction enzyme BamHI.

1–14) 1 Kb DNA ladder; 2–4) clones 1, 2 and 3: preculture; 5–7) clones 1, 2 and 3: I culture; 8–10) clones 1, 2 and 3: II culture; 11–13) clones 1, 2 and 3: III culture.

FIG. 4

Electrophoretic analysis of the total proteins extracted from B.subtilis SMS003 transformed with pSM671 containing genes encoding for different heterologous proteins.

A) pSM671 + gene of carbamylase of A. radiobacter. (1) purified carbamylase, (2) SMS003 (pSM671/carbamylase).

B) pSM671 + gene of the recombinant anti α hCG ScFv antibody. (1) purified anti α hCG ScFv, (2) SMS003 (pSM671), (3) SMS003 (pSM671/anti α hCG ScFv).

C) pSM671 + gene of the human growth hormone (hGH). (1) SMS003 (pSM671), (2) purified hGH, (3) SMS003 (pSM671/hGH).

D) pSM671 + gene of interleukin-1β (IL-1β). (1) SMS003 (pSM671), (2) standard molecular weights, (3) purified IL-1β, (4) SMS003 (pSM671/Il-1β).

E) pSM671 + gene of the natural antagonist of IL-1β(Il-1rα). (1) SMS003 (pSM671, (2) SMS003 (pSM671/Il-1rα), the protein of interest is indicated by the arrow.

The following experimental examples provide a better illustration of the present invention without restricting it in any way.

EXAMPLE 1

Construction of the cloning vector pSM671

A) Insertion into pSM143 of a synthetic promoter and the multiple cloning site of pUC18.

Figure 1A:
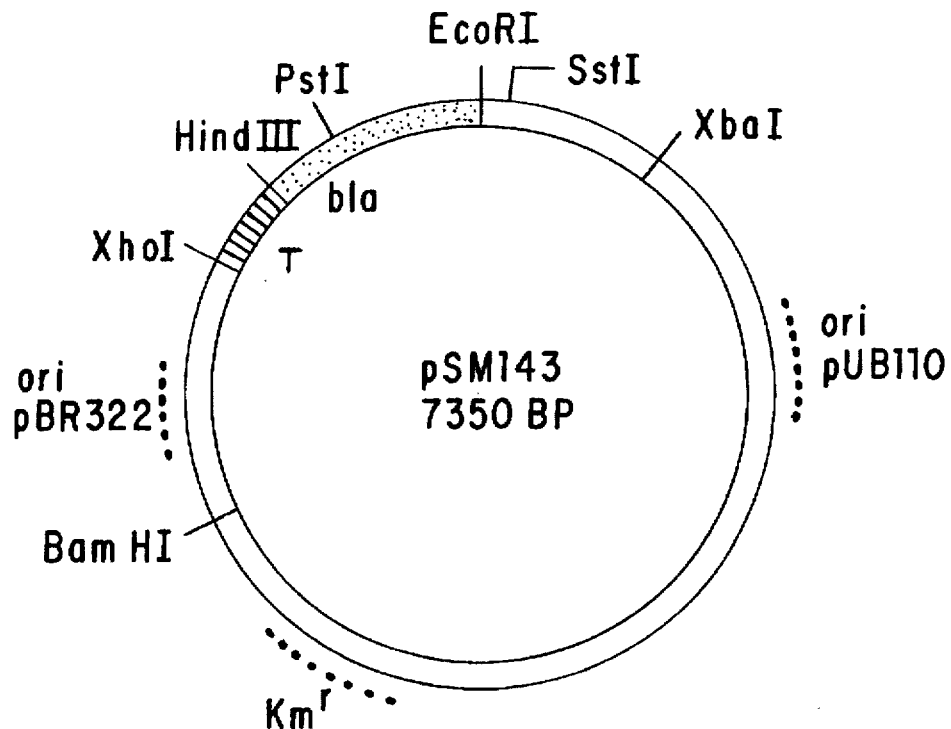
FIGS. 1A–B

1 μg of the plasmid pSM143 (ATCC 53038) (FIG. 1A) was resuspended in 20 μl of a buffer solution containing 10 mM Tris-HCl pH 8.0, 5 mM MgCl$_2$, 100 mM NaCl, 1 mM μ-mercaptoethanol, 2 U of each of the restriction enzymes XbaI and HindIII (Boehringer). The reaction was carried out at 37° C. for 1 hour and then inactivated at 65° C. for 10 minutes.

Operating in this way two fragments were obtained, of about 5700 bp and 1650 bp respectively, the latter containing the promoter region of resistance to erythromycin of pE194 and the Bla gene which gives resistance to Ampicillin. The fragment of 5700 bp was purified by electroelution on agarose gel at 0.8% (Sambrook et al., Molecular Cloning: a laboratory manual, 1989). At the same time a polynucleotide, whose sequence is indicated below, was synthesized (SEQ ID NOS:2 and 3)

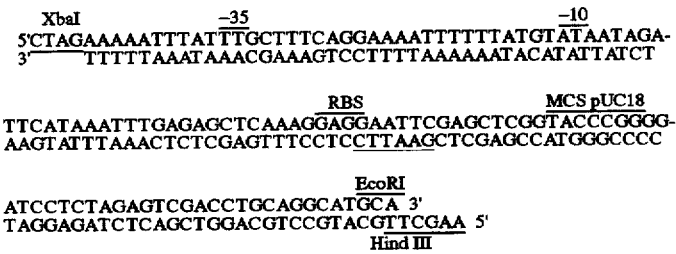

This synthetic polynucleotide contains: (i) a sequence which acts as strong promoter, capable of directing with great efficiency the transcription of the messenger RNA, (ii) the bond site of the mRNA to the ribosome (RBS) and the multiple cloning site (MCS) of the plasmid pUC18 (Boehringer).

10 ng of the fragment XbaI-HindIII of 5700 bp and 10 ng of the synthetic polynucleotide were suspended in 20 μl of buffer solution containing 66 mM Tris-HCl pH 7.5, 5 mM MgCl$_2$, 1 mM dithiotreitol (DTT), 1 mM ATP and ligated in the presence of 0.1 U of T4 DNA ligase at 16° C. for 18 hours.

E.coli HB101 cells (BRL), made competent according to the method described by Mandel and Higa (1970), (J. Mol. Biol., 53:159–162) were transformed with 2 μl of the ligation mixture and the transformants were selected on LB agar plates (Bacto Triptone 10 g/l, yeast extract 5 g/l, NaCl 10 g/l, 16 g/l agar) containing 5 μl/ml of Kanamycin.

The plasmid DNA was extracted from a Km$^r$ colony and sequenced according to the method of Sanger F. et al. (1977) (Proc. Natl. Acad. Sci. USA, 74: 5463).

It was therefore possible to verify the exact insertion in pSM143 of the synthetic polynucleotide, in the place of the region which comprised the promoter of resistance to erythromycin of pE194 and the Bla gene. The new plasmid was called pSM143-A.

B) Insertion of the DNA fragment of pSM213 containing the CAT gene and the synthetic terminator t$_O$ lambda into pSM143-A.

Figure 1B:
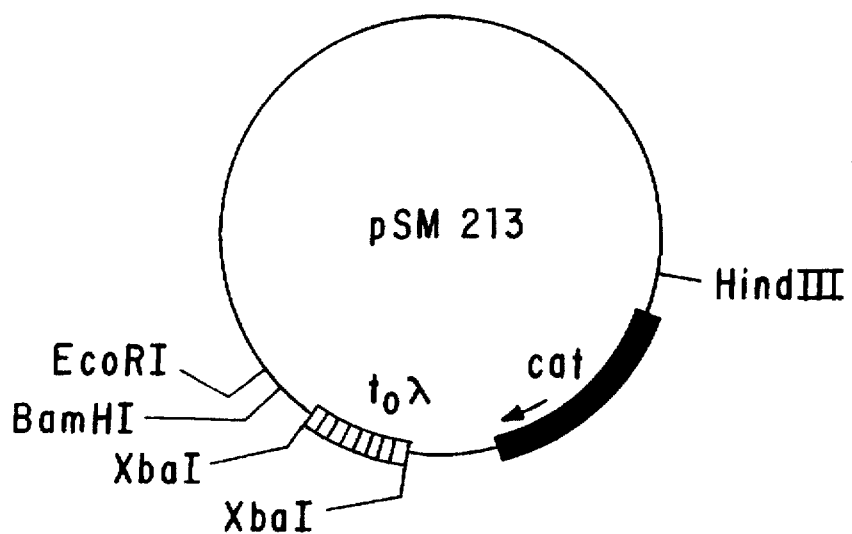

10 μg of the plasmid pSM213 (FIG. 1B), described in Italian patent application No. 19,551 A/87, were digested with 30 U of the BamHI enzyme (Boehringer) in 100 μl of buffer solution containing 10 mM Tris-HCl pH 8.0, 5 mM MgCl$_2$, 100 mM NaCl, 1 mM β-mercaptoethanol, at 37° C. for 1 hour.

The reaction was inactivated by extracting the digestion mixture with an equal volume of phenolo-chloroform and isoamylic chloroform-alcohol; the DNA was then precipitated, separated and dried under vacuum.

The DNA thus obtained was resuspended in 250 μl of buffer solution containing 50 mM Tris-HCl pH 7.2, 10 mM MgSO$_4$, 0.1 mM DTT, 50 μg/ml BSA, 80 μM of dGTP, 80 μM of dATP and 10 U of polymerase Klenow DNA. The resulting mixture was incubated at room temperature (20°–25° C.) for 30 minutes and then inactivated with EDTA 25 mM and the proteins extracted with phenolo-chloroform and isoamylic chloroform-alcohol.

The DNA was precipitated from the aqueous phase, separated by centrifugation, dried under vacuum and finally resuspended in 200 μl of buffer solution containing 10 mM Tris-HCl pH 8.0, 10 mM NaCl, 5 mM MgCl$_2$, 1 mM β-mercaptoethanol and 20 U of restriction enzyme HindIII (Boehringer). The digestion reaction was carried out at 37° C. for 1 hour and subsequently inactivated at 65° C. for 10 minutes.

The whole digestion mixture was then charged onto polyacrylamide gel at 6% and run at 120 Volts for 3 hours.

The DNA fragment corresponding to the band of about 1000 bp, containing the Cat gene without its promoter and terminator t$_O$ of the lambda bacteriophage, was electroeluated as described by Maxam and Gilbert (Methods in Enzymology (1980), vol. 65, 499–560).

10 μg of pSM143-A were contemporaneously digested with 30 U of the restriction enzyme XhoI (Boehringer) in 100 μl of buffer solution containing 50 mM Tris-HCl pH 7.52, 10 mM MgCl$_2$, 100 mM NaCl, 1 mM DTT, at 37° C. for 1 hour. After the reaction had been inactivated at 65° C. for 10 minutes, the DNA was precipitated, separated and then resuspended in 250 μl of buffer solution containing 50 mM Tris-HCl pH 7.2, 10 mM MgSO$_4$, 0.1 mM DTT, 50 μg/ml BSA, 80 μM of dGTP, 80 μM of dATP and 10 U of polymerase Klenow DNA. The resulting mixture was incubated at room temperature (20°–25° C.) for 30 minutes and then inactivated with EDTA 25 mM and the proteins extracted with phenolo-chloroform and isoamylic chloroform-alcohol. The DNA was precipitated from the aqueous phase, separated by centrifugation, dried under vacuum and finally resuspended in 200 μl of buffer solution containing 10 mM Tris-HCl pH 8.0, 10 mM NaCl, 5 mM MgCl$_2$, 1 mM β-mercaptoethanol and 20 U of restriction enzyme HindIII. The digestion reaction was carried out at 37° C. for 1 hour and subsequently inactivated at 65° C. for 10 minutes.

Two DNA fragments of 5600 by and 250 bp respectively were thus obtained, the latter containing the terminator of the bacteriophage fd; the 5600 bp fragment was purified by electroelution on agarose gel at 0.8%.

2 μg of this fragment were ligated with 1 μg of the 1000 bp fragment deriving from pSM213. The reaction was carried out in 100 μl of buffer solution containing 66 mM Tris-HCl pH 7.5, 5 mM MgCl$_2$, 1 mM dithiotreitol (DTT), 1 mM ATP and bound in the presence of 2.0 U of T4 DNA ligase at 16° C. for 18 hours.

Competent cells of E.coli 71/18 (Messing, J.B. et al. (1977) Proc. Natl. Acad. Sci. USA, 74: 3642) were transformed with different amounts of the ligation mixture and the transformants were selected on plates of LB agar containing 5 μg/ml of Kanamycin and 20 μg/ml of Chloramphenicol.

A plasmid, whose restriction map was defined, was isolated, by a rapid process, from a Km$^r$ Cm$^r$ colony.

Figure 2:
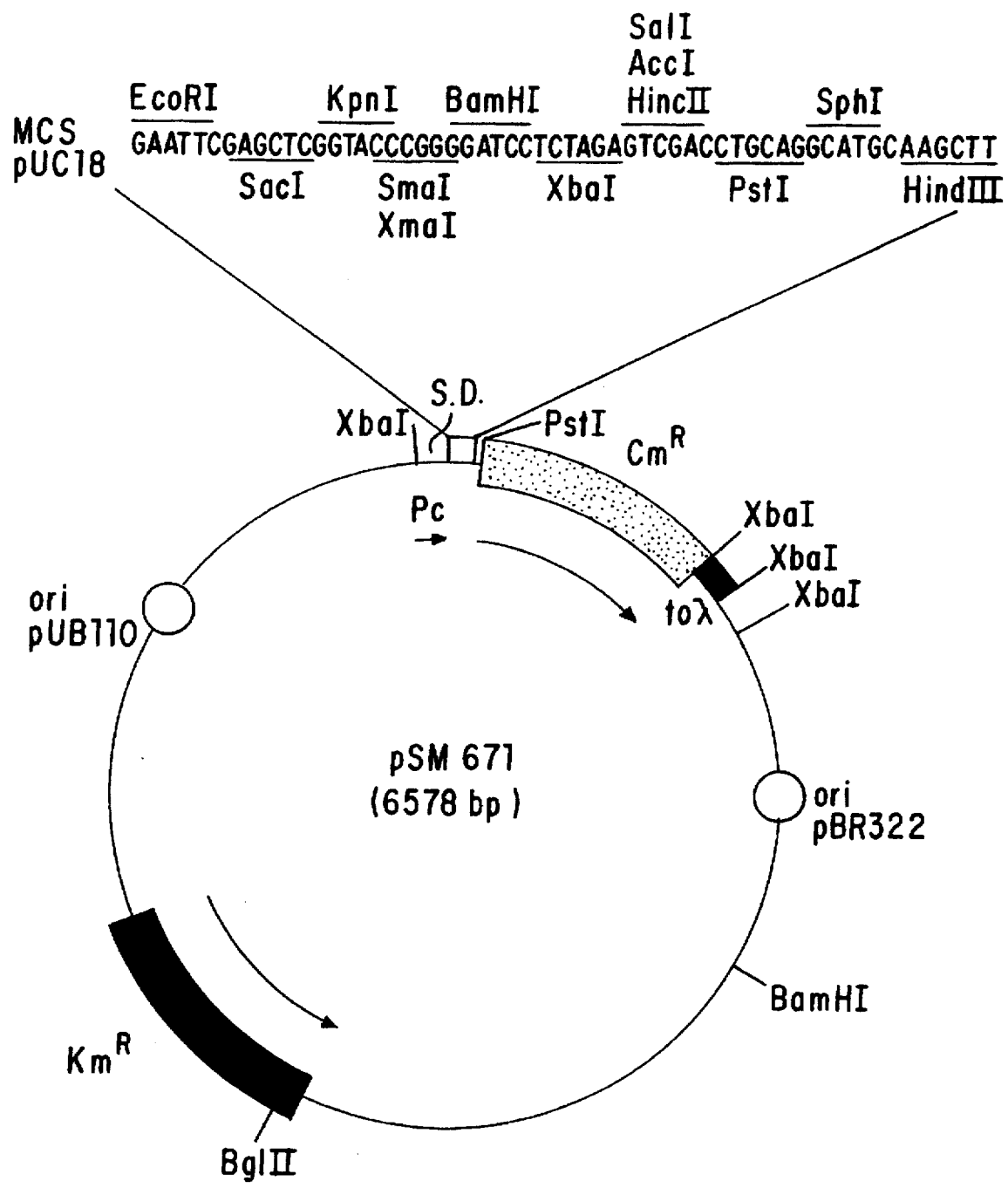

The sequence analysis of this plasmid showed the expected characteristics, or the presence of the synthetic promoter, RBS site, multiple cloning site of puC18, the Cat gene, lambda terminator t$_O$ and double resistance to the antibiotics kanamycin and Chloramphenicol. This plasmid was called pSM671 (FIG. 2). The clone of E.coli containing said plasmid was marked with the abbreviation SMC309.

The plasmid pSM671 was then used to transform cells of B.subtilis SMS003 NRLLB 15897, made competent as described by Contenete and Dubnau, (1979), (Mol. Gen. Genet., 167, 251–258). The selection of the transformants was carried out by plating on a Tryptose Blood Agar Base (TBAB) medium of DIFCO, containing 5 μg/ml of Kanamycin and 5 μg/ml of Choramphenicol.

EXAMPLE 2

Control of the segregational and structural stability of the vector pSM671

A) Segregational stability

The purpose of this experiment is to verify the stability of the plasmid pSM671 in the transformed strains of *E.coli* and *B.subtilis* after a prolonged period in culture.

Three independent clones of *E.coli* SMC309 were cultured at 37° C., 200 rpm for 16 hours in 100 ml flasks, containing 10 ml of LB medium (Bacto Triptone 10 g/l, yeast extract 5 g/l, NaCl 10 g/l), containing 20 mg/ml of Choramphenicol.

Three independent clones of *B.subtilis* SMS003, transformed with pSM671, were contemporaneously cultured at 37° C., 200 rpm for 16 hours in 100 ml flasks, containing 10 ml of VY medium (yeast extract 5 g/l, veal infusion broth 25 g/l), containing 5 mg/ml of Choramphenicol.

The three cultures of both the microorganisms (0.1 ml) were used to inoculate a further 10 ml of the same mediums plus antibiotic. The new cultures were cultured at 37° C., 200 rpm for 16 hours and this process was repeated for a further two times; the cellular growth was followed as an increase in the optical density measured at 600 nm (O.D.$_{600}$).

At the end of the experiment, aliquots of the cultures were removed, suitably diluted and then plated on the following mediums:

LB agar +/− 20 mg/ml Chloramphenicol (*E.coli*)

VY agar +/− 5 mg/ml Chloramphenicol (*B.subtilis*).

The plates were incubated at 37° C. for 16 hours and then the colonies (CFU/ml) grown with or without the antibiotic were counted. In this way it was possible to determine the percentage of cells which had maintained the plasmid and were therefore Cm$^r$.

TABLE 1

| Strain | CFU/ml −Cm | CFU/ml +Cm | %Cm$^r$ |
|---|---|---|---|
| 71/18 | 9.2 × 10$^8$ ± 0.3 | 8.9 × 10$^8$ ± 0.2 | 97 |
| SMS 003 | 4.5 × 10$^8$ ± 0.2 | 4.4 × 10$^8$ ± 0.3 | 98 |

As shown in table 1 (average of three experiments ± SD) the plasmid is maintained in more than 95% of the cellular population, thus showing a considerable segregational stability even after subsequent passages in culture.

B) Structural stability

At the end of each single passage (16 hours of culture) aliquots of each of the cultures of *E.coli* and *B.subtilis* were collected and normalized for O.D.$_{600}$. From the equivalent of 1.5 ml of culture at O.D.$_{600}$ =3.0, the plasmid DNA was extracted, by alkaline lysis (Sambrook et al., Molecular Cloning: a laboratory manual, 1989) and then purified on QIAGEN$^R$ type 20 columns (Promega). The DNAs obtained were digested with 1 U of the enzyme BamHI (Boehringer) in 10 μl of buffer solution containing 10 mM Tris-HCl pH 8.0, 5 mM Mgcl$_2$, 100 mM NaCl, 1 mM β-mercaptoethanol. The reaction was carried out at 37° C. for 1 hour and subsequently inactivated at 65° C. for 10 minutes.

Figure 3A:
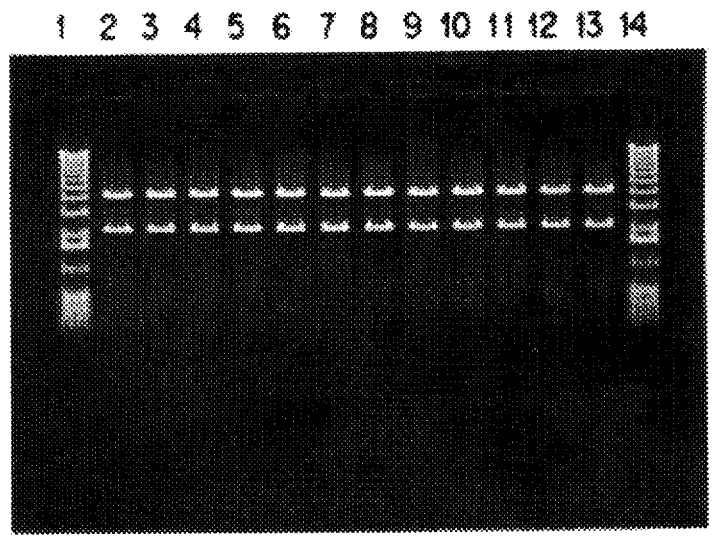
Figure 3B:
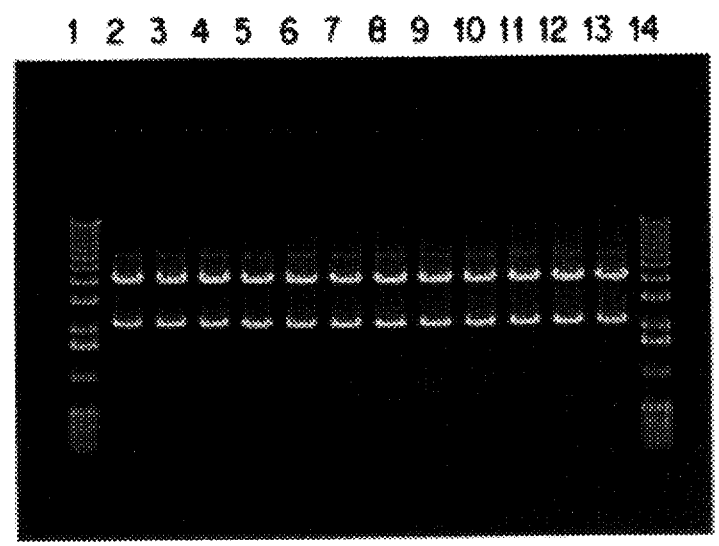
Figure 4A:
Figure 4B:
Figure 4C:
Figure 4D:
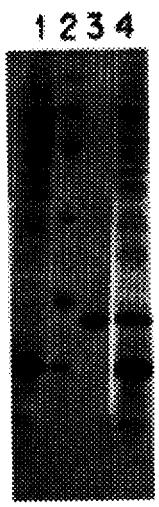
Figure 4E:

The digested plasmids were charged onto agar gel and run for 2 hours at 90 V, 90 mA; the gels were coloured with ethidium bromide 1 mg/ml and then visualized on a transilluminator with UV light. As shown in FIG. 3A and 3B, the cut with the restriction enzyme BamHI produces the expected bands of about 4300 and 2300 bp even after various generations of liquid culture, showing that pSM671 is structurally stable both in *E.coli* and in *B.subtilis*.

EXAMPLE 3

Expression of recombinant proteins in *B.subtilis*

To verify the expression capacity of this vector, the genes which encode for: *Agrobacterium radiobacter* carbamylase, a recombinant anti human chorionic α-gonadotropin single chain antibody (hGH), interleukin-1β, (IL-1β) and the natural antagonist of IL-1β (IL-1rα)) were cloned in the restriction sites EcoRI/HindIII or EcoRI/PstI of pSM671. The recombinant vectors obtained were used to transform cells of *B.subtilis* SMS003. The Cm$^r$ transformants, selected as described in example 1, were then cultivated in 10 ml of VY medium to which 5 μg/ml of chloramphenicol had been added. The flasks were incubated, under stirring (200 rpm), at 37° C. for 16 hours.

1 ml of culture for each transformant was collected by centrifugation (12,000 rpm for 2 minutes at 4° C., in a microcentrifuge). The cells were washed with 1 ml of: 20 mM Tris-HCl pH 7.5, 2 mM EDTA and then resuspended in 150 ml of: 50 mM Tris-HCl pH 7.2, 15% sucrose, 1–2 mg/ml lysozyme. The samples were incubated at 37° C. for about 10 minutes. 150 ml of "SAMPLE BUFFER 2x" (125 mM Tris-HCl pH 6.8, 20% glycerol, 4% sodiumdodecylsulphate (SDS), 4% β-mercaptoethanol, 0.02% bromophenol blue (BBF)) were then added to the cellular suspension. The samples were boiled for 5 minutes and then 20 ml of the extracts (equal to 67 ml of culture) were charged onto a polyacrylamide gel at 12.5% and separated by SDS-PAGE (Laemmli, U.K. (1970) Nature, 227: 680) for 3 hours at 30 mA.

After the electrophoresis the gels were coloured with Comassie Brilliant Blue R250 and the expression of the proteins of interest was thus verified as illustrated in FIG. 4.

---

We claim:

1. A plasmid vector stable in *Escherichia coli* and *Bacillus subtilis* comprising a synthetic promoter which directs expression of a heterologous gene put under its control, wherein said plasmid vector is deposited at the Centraalbureau Voor Schimmelcultures as number CBS 205.94.

2. The plasmid vector in accordance with claim 1, further comprising a heterologous gene encoding a prokaryotic polypeptide selected from the group consisting of enzymes hydantoinase, carbamylase, α-amylase, β-amylase, and isoamylase, or a eukaryotic polypeptide selected from the group consisting of interleukin, interferon, hormones, and recombinant antibodies.

3. A microorganism selected from the group consisting of *Escherichia coli* and *Bacillus subtilis* transformed with the plasmid vector of claim 1.

4. The microorganism in accordance with claim 3, which is *Escherichia coli* SMC309 CBS 205.94.

5. A method for the production of heterologous proteins comprising transforming a strain of *Bacillus subtilis* and/or *Escherichia coli* with the plasmid vector in accordance with claim 1, culturing said transformed strain and isolating said proteins from said transformed strain.

6. The plasmid vector of claim 1, wherein said synthetic promoter has the sequence 5' CTAGAAAAAT TATTTGCTT TCAGGAAAAT TTTTTATGTA TAATAGATT 3' (SEQ ID NO:1).

* * * * *